Figure 1:
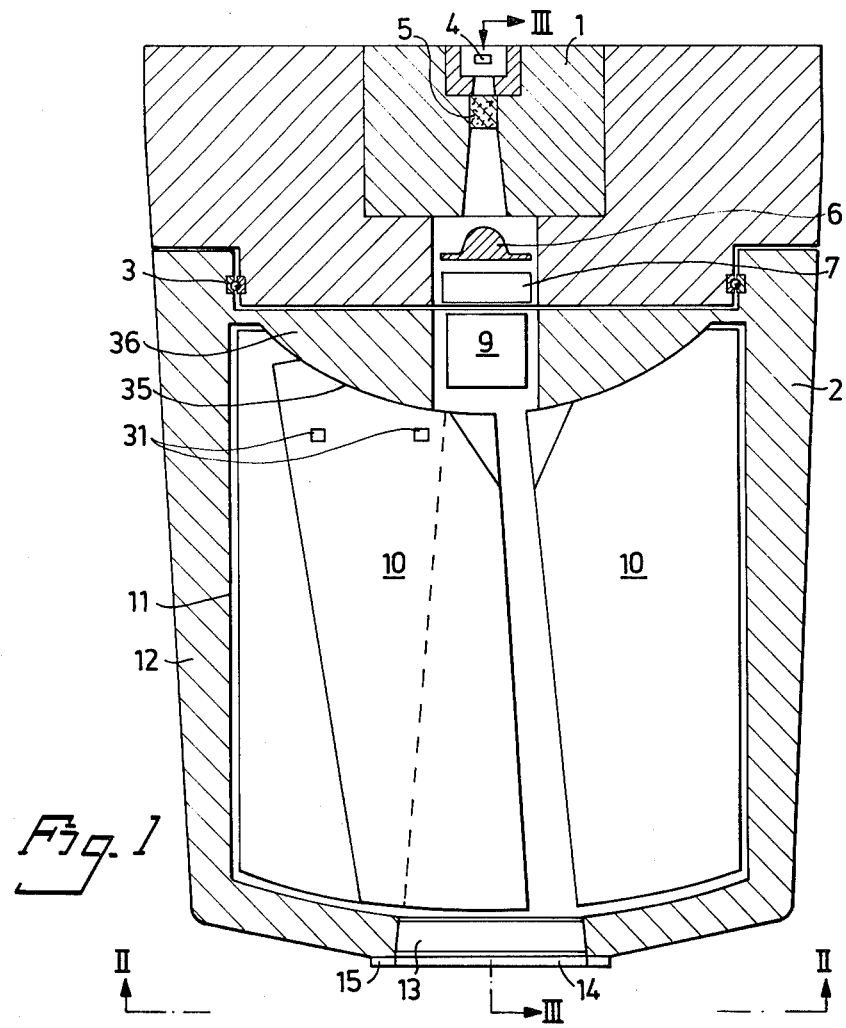

United States Patent [19]

Brahme

[11] Patent Number: 4,463,266
[45] Date of Patent: Jul. 31, 1984

[54] NEUTRON COLLIMATOR
[75] Inventor: Anders Brahme, Bromma, Sweden
[73] Assignee: Instrument AB Scanditronix, Sweden
[21] Appl. No.: 236,199
[22] Filed: Feb. 20, 1981
[51] Int. Cl.³ .............................................. G21K 1/04
[52] U.S. Cl. ................................. 250/505.1; 378/150; 378/153; 378/206
[58] Field of Search .............. 250/505, 511, 512, 251, 250/492.1, 513, 514, 515, 509; 378/206, 150, 153

[56] References Cited

U.S. PATENT DOCUMENTS

| | | | |
|---|---|---|---|
| 1,484,663 | 2/1924 | Mutscheller | 250/509 |
| 1,976,179 | 10/1934 | Mannl | 378/206 |
| 2,844,736 | 7/1958 | Johns et al. | 250/512 |
| 3,487,218 | 12/1969 | Krebs et al. | 378/153 |
| 3,715,597 | 2/1973 | Hofmann et al. | 250/518.1 |
| 3,805,081 | 4/1974 | Barthel et al. | 378/150 |
| 3,995,163 | 11/1970 | Colditz | 250/518.1 |
| 4,324,979 | 4/1982 | Bowley et al. | 250/505 |

FOREIGN PATENT DOCUMENTS 192300 12/1906 Fed. Rep. of Germany ...... 250/514

OTHER PUBLICATIONS

Barnes et al., "The Scanning Grid: A Novel and Effective Bucky Movement", Radiology, 135, Jun. 1980, pp. 765-767.

Primary Examiner—Alfred E. Smith
Assistant Examiner—Carolyn E. Fields
Attorney, Agent, or Firm—Lewis H. Eslinger

[57] ABSTRACT

A neutron collimator with an adjustable irradiation field for an effective neutron radiation source includes a protective radiation casing; a frame surrounded by the casing; a plurality of individual carrier arms mounted on the frame; a plurality of pairs of opposite elongated wedge-shaped slabs arranged side by side such that respective ones of the opposite wedge-shaped slabs form a fan-shaped configuration which converges toward an apex at the neutron radiation source, each wedge-shaped slab being mounted for rotational and translational movement on a respective carrier arm such that the wedge-shaped slabs of each pair are mounted for motion towards and away from each other along a path which intersects the irradiation field for the neutron radiation source and such that the inner side surface of each wedge-shaped slab is always directed generally towards the neutron radiation source; and at least one bearing provided between each wedge-shaped slab and the respective carrier arm on which it is movably mounted.

13 Claims, 5 Drawing Figures

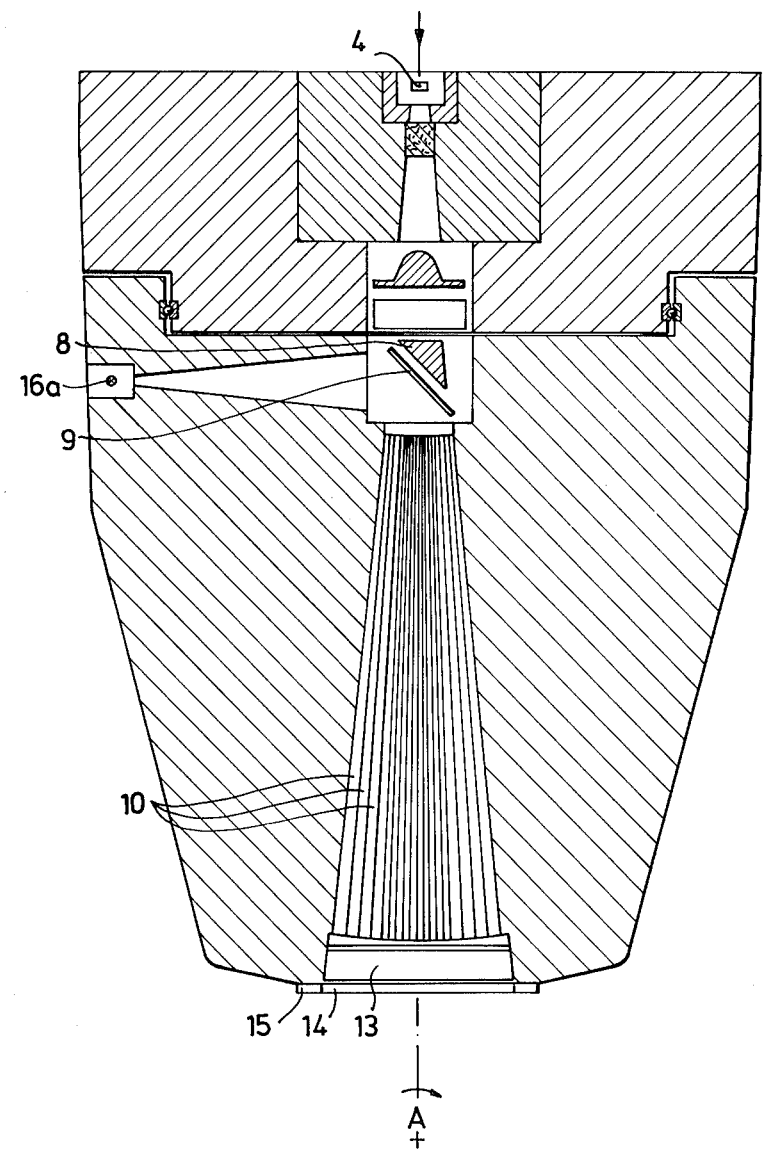

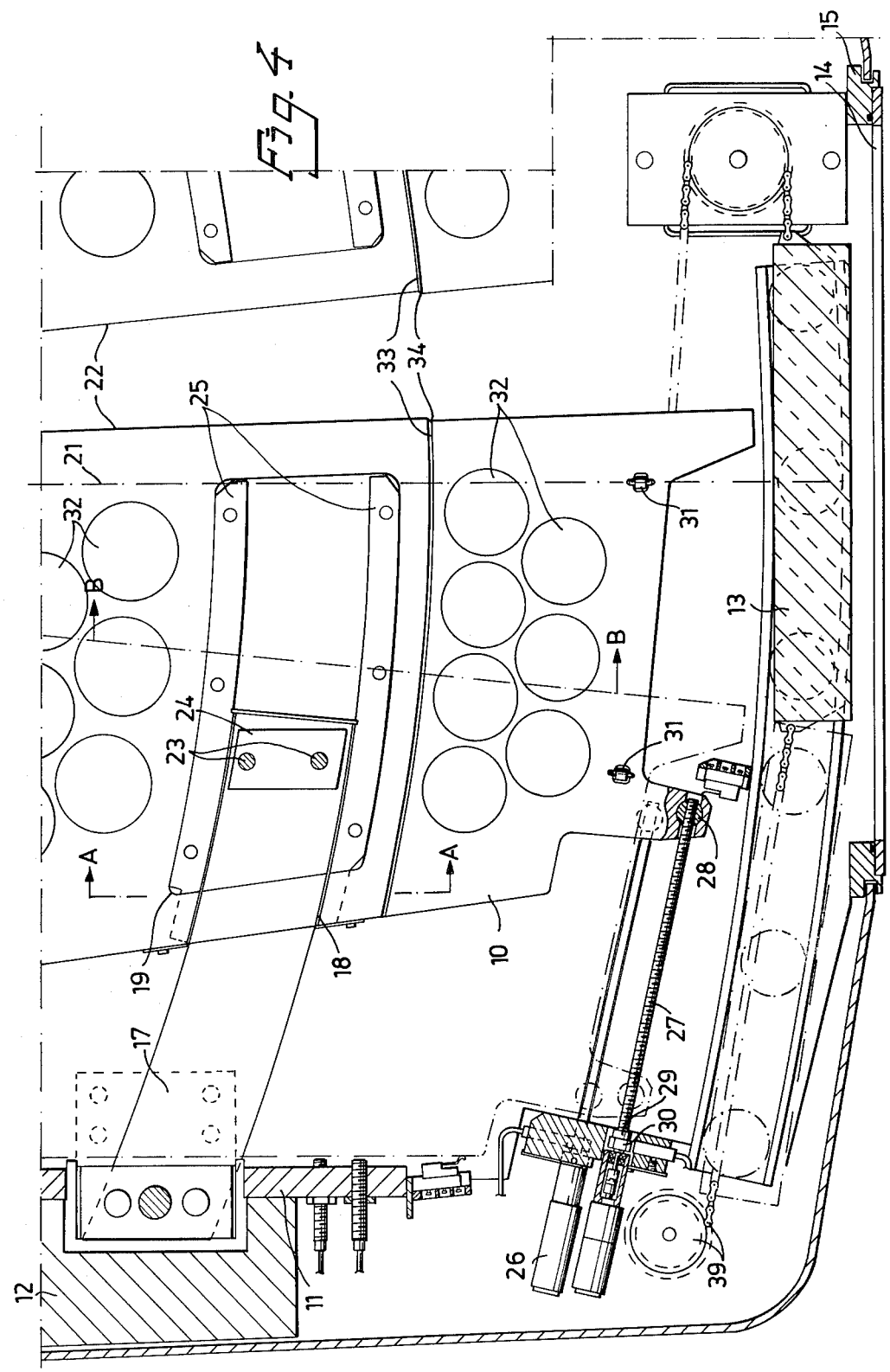

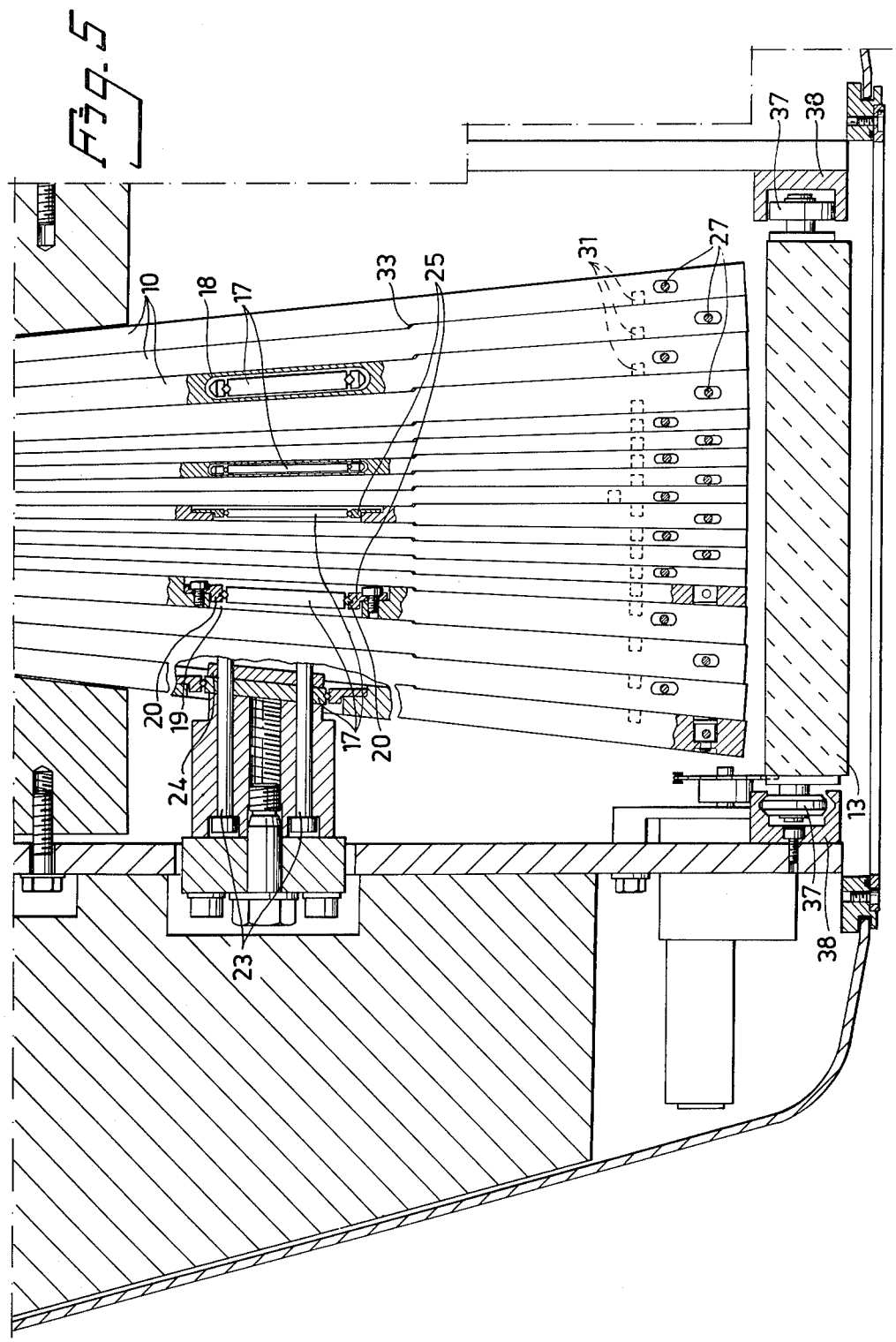

NEUTRON COLLIMATOR

The present invention relates to a neutron collimator with adjustable irradiation field. A neutron collimator of this kind is disclosed in our Swedish patent application No. 79.05167-8. Said patent application discloses neutron absorbing blocks which may be shaped as a number of separate wedge-like slabs. The present invention is an improvement of this previously known collimator and relates particularly to the orientation and motion of the slabs. In accordance with the present invention the wedge-like slabs are arranged side by side to form a fan-like configuration the (imagined) apex of which generally is at the effective neutron radiation source. Separate carrier means are provided which upon motion of the slabs impart the latter a transitional as well as a rotational movement of the kind that the inner side surface of each slab is pointing generally at said effective neutron radiation source for each setting of the slabs. Thanks to this "double focusing" of the slabs on the effective neutron radiation source an optimum, that is as sharp as possible, penumbra is obtained along the irradiation field rand.

In accordance with the invention individual carrier means are provided for each slab thereby allowing individual setting of each slab.

In accordance with another aspect of the invention each pair of opposite slabs can be closed together not only in the plane which contains the central beam from the effective neutron radiation source and which is perpendicular to all slab motion directions but also in planes which are parallel with said plane and which are displaced sideways in relation thereto. Non-centered dose distributions may therefore be obtained. Moreover it is possible to prevent therapy radiation from reaching areas, the spine for example, which should not be irradiated when the effective neutron radiation source is rotated around the patient because the center of rotation of the effective neutron radiation source will be blocked by the collimator in accordance with the invention.

Figure 2:
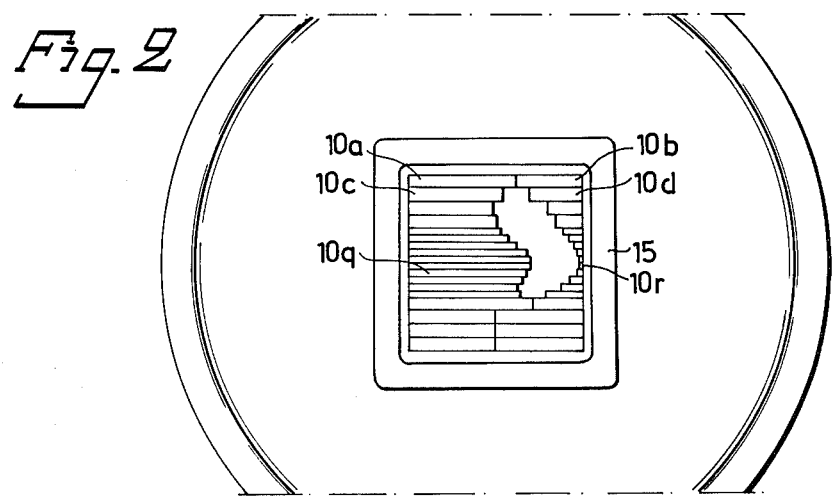

An embodiment of the invention will be described in detail below the reference to the accompanying drawings in which FIG. 1 is a cross-sectional view of the neutron collimator in accordance with the invention, FIG. 2 is a front view, partially a broken way, of the collimator shown in FIG. 1, said front view being taken along lines II—II in FIG. 1, FIG. 3 is cross-sectional view along line III—III in FIG. 1, FIG. 4 is a detailed view, shown in enlarged scale, of the carrier means for the left slab shown in FIG. 1 and FIG. 5 is a partial plane view and a partial section view of the device shown in FIG. 4.

The general construction of the neutron collimator in accordance with the invention will now be described with reference to FIGS. 1-3. The collimator comprises a stationary collimator 1 and a continuously variable collimator 2. A bearing 3 rotatably connects units 1 and 2 to each other. The stationary collimator is enclosing an effective neutron radiation source 4 from which high energy neutrons are emitted. The neutrons will hit a filter 5 increasing the average energy of the neutron beam and a flattening filter 6 in the indicated order before they pass a ionisation chamber 7 in which the intensity of the beam is measured. From this chamber the neutrons will enter the continuously variable collimator 2 in which they pass a wedge filter 8 (compare FIG. 3), an inclined mirror 9 and finally a number of settable collimator slabs 10 of neutron absorbing material. The slabs 10 are supported on carrier means, not shown in FIGS. 1-3, mounted in a frame 11. Frame 11 is surrounded by a casing 12 of a low density, high hydrogen atom content material, for example polyethylene. Said casing 12 is surrounded by a thin layer of lead, not shown in detail, or of some other high atomar material serving as gamma radiation protection. Gamma radiation is generated when neutrons are absorbed in casing 12. A similar protection against gamma radiation is provided by a lead glass slab 13 arranged in the bottom section of frame 11. The therapy neutron radiation is leaving the collimator through a protective window 14 attached to a frame 15.

The irradiation field leaving the collimator is adjustable and continuously variable with collimator slabs 10. An example of the collimator slab setting producing an irradiation field formed as a kidney is shown in FIG. 2. FIG. 2 is also disclosing that the collimator slabs 10 are arranged in pairs of opposite slabs, slab 10a opposite slab 10b, 10c opposite 10d etc. The collimator slabs are mounted for motion towards and from each other. Each slab can be set separately. In FIG. 2 slabs 10a and 10b are in abutting relationship, that is they are closed together, while the pair of slabs 10c-10d has been set with little space therebetween through which space the neutron radiation may pass unobstructed. FIG. 2 is also disclosing that the central neutron beam from the effective neutron radiation source as well as beams close to the central beam may be blocked, that is absorbed, by slab 10q and slabs adjacent thereto. This is advantageous when a patient is subjected to arc therapy i.e. the collimator is rotated around the patient, because a volume, e.g. the spine, which should not be subjected to the central beam is, in accordance with the invention positioned at the centre of rotation of the effective neutron radiation source 4. This centre of rotation has been marked with A in FIG. 3.

In FIG. 2 it is also shown that slabs 10 have different thickness. Central slabs 10q-10r and slabs adjacent thereto are thinner than the outer slabs 10a-10b. In accordance with an embodiment of the present invention all slabs may be of the same thickness and in an alternate embodiment the thickness of the slabs may be further differentiated.

In FIG. 3 it is clearly shown that the slabs have the form of a wedge and that they are arranged side by side to form a fan-like configuration the imagined apex of which is positioned generally at the effective neutron radiation source 4.

In FIG. 3 it is also shown that the irradiation field can be made visible on the patient by using a lamp 16a the light of which is reflected by an inclined mirror 9 from which the light is passing down through the collimator opening as set in order to strike the area to be subjected to the neutron radiation. The mirror image of lamp 16a is positioned at a point which generally corresponds to the position of the effective neutron radiation source 4.

In FIGS. 4 and 5 the detailed construction of a preferred embodiment of the slab carrier means comprises an arm 17 extending into an aperture 18 provided in one of the side surfaces of each slab 10. Aperture 18 is extending a small distance into the mid-section of the slab and is opening into a through opening 19. Through opening 19 is extending between the two main surfaces of each slab. In through opening 19 bearing means 20 are provided, one bearing means on each side of the arm. Accordingly, the slab can be moved along the arm. In the shown embodiment said bearing means comprise rolls and the slab may therefore be rolled with low friction along a path which intersects the irradiation filed from the effective neutron radiation source 4.

In FIG. 4 dash dotted line 21 represents the central beam from the radiation source. As is apparent from this Figure the inner side surface 22 of slab 10 can be moved towards and beyond the central beam 21.

Aperture 18 and arm 17 are so positioned that the arm is supporting the slab in the vicinity of the centre of gravity of the slab. In doing so the weight of the slab is counterbalanced and only a small force is required in order to move the slab along the arm.

As is apparent from FIG. 4 arm 17 is curved upwardly. Bearing means 20 and through opening 19 have a corresponding curvature. The curvature is so selected that when moving the slab along the arm the slab will also rotate around a centre of rotation positioned at or in the vicinity of the effective neutron radiation source 4. The inner side surface 22 of the slab will therefore always be directed generally toward or in-line with the effective neutron radiation source. The last-mentioned feature in combination with the fan-like configuration of the slab assembly indicates that the slabs are twice or double focused generally at the effective neutron radiation source. This double focusing brings about an optimum, that is as sharp as possible, penumbra along the band regions of the irradiation field.

In order to ensure a mechanically rigid construction the outer free ends of each arm 17 are interconnected with the aid of rods 23 and distance means 24. Rods 23 are extending through said through openings 19 of each slab 10.

In the embodiment shown bearing means 20 comprise roller ways which are curved in accordance with the curvature of the arm. Each roller way includes two opposite slots having a square cross section. One of the slots is provided in the arm, the other in a mounting bracket 25 which is attached to a lip provided in the through opening 19. In the roller ways a number of cylindrical rollers are provided the central axes thereof lying in parallel planes but rotated 90° to each other. Instead of roller ways other friction reducing bearing means may be used, for example ball bearing ways, rollers provided in slots with trapezoidal cross section etc. In FIG. 5 the cross sections of arms 17 extending into slabs 10 are taken at different locations along the arm. In the third slab from the right in FIG. 5 aperture 18 and the web portions of the slab surrounding this aperture are clearly shown. The cross section has been taken along lines A—A in FIG. 4. The cross section shown in the fourth slab from the left in FIG. 5 has been taken along lines B—B in FIG. 4.

The position of the slabs along the arms are individually settable with a setting device. In the embodiment shown this device comprises an electrical motor 26 which when energized rotates a screwed rod 27 on which a nut 28 is screwed. Said nut is ball-shaped and is rotatably journalled in the bottom portion of slab 10. The motor 26 is hinged in a pivot 29 attached to frame 11. An inductive pick-up device 30 is surrounding the screwed rod and is transmitting a predetermined number of electrical pulses for each revolution of the rod. A counter is counting said pulses and the count thereof is converted into a measure representing the distance between the central beam 21 and a predetermined point provided on the slab. Instead of the setting device as shown a wire and pulley system may be used. Also pneumatic or hydraulic setting devices may be used instead of the electrical motor.

To prevent adjacent main surface of the slabs from jamming when a slab is moved along the arm the upper and bottom section of each slab is provided with a number of friction reducing means in the form of rollers 31 extending only a small distance above only one main surface of each slab. In FIGS. 4 and 5 the bottom section rollers are shown and in FIG. 1 the positions of the corresponding upper section rollers are illustrated.

Slabs 10 are manufactured from neutron absorbing material. The upper section of the slabs are manufactured from tungsten and the bottom section comprises low carbon soft iron, for example Armco-steel or steel. The slabs are provided with a number of through openings 32 generally completely filled with a material having low density but high hydrogen atom content, for example polyethylene. Two objects are achieved therewith, namely reducing the weight of the slabs and thermalizing (retarding) the neutrons.

Several measures have been taken to prevent neutrons from escaping the collimator. In order to prevent a direct stray flux between the slabs stacked together side by side the top and bottom sections of the main surfaces of the slabs are provided with steps 33. In FIGS. 4 and 5 only the bottom steps are shown. The steps provided in one main surface of a slab are matching corresponding complementary steps provided in the main surface of an adjacent slab. In order to prevent stray neutron flux between two closed (abutting) slabs, for example slabs 10a and 10b in FIG. 2, the inner surface 22 of each slab is likewise provided with steps 34. The steps 34 provided on the inner side surface of one slab are matching complementary shaped steps 34 provided in the side surface of the opposite slab. To prevent stray neutron flux in the region above the upper surface of the slabs said upper surface 35, shown in FIG. 1, has been curved and in the adjacent bottom section of collimator 2 a body 36 of neutron absorbing material has been provided, said body having a shape which is matched to the shape of the curved surface 35. The body 36 is of the same material as the casing 12.

During the neutron radiation therapy treatment lead glass slab 13 must be moved away from the window 14 and to this end it is movably supported on rollers 37 supported in guides 38 which are attached to the bottom section of frame 11. The position of lead glass slab 16 is set with for example a chain and sprocket wheel system 39 (compare FIG. 4).

In accordance with another embodiment of the invention each arm 17 is omitted and instead bearing means, for example rollers, are provided below the bottom surface of each slab. In this embodiment the bottom surface of each slab is curved and is provided with a longitudinal, in cross section trapezoidal, slot in which the rollers are running. The rollers are resting against a curved surface provided on a support attached to the bottom section of the frame. The centre of curvature of the bottom surface of the slabs and of the curved surface of the opposite supports are at or in the vicinity of the effective neutron radiation source 4. When a slab is moved it is imparted a translational as well as rotational motion.

The various embodiments described above may be modified and varied within the scope of the accompanying claims.

I claim:

1. A neutron collimator with an adjustable irradiation field for an effective neutron radiation source, comprising:

support means including a plurality of individual carrier means;

frame means in which said support means is mounted;

protective radiation casing means surrounding said frame means;

a plurality of pairs of opposite elongated wedge-shaped slabs arranged side by side such that respective ones of said opposite wedge-shaped slabs form a fan-shaped configuration which converges toward an apex at said neutron radiation source, each wedge-shaped slab having an inner side surface and being mounted for rotational and translational movement on a respective one of said individual carrier means such that the wedge-shaped slabs of each pair are mounted for motion towards and away from each other along a path which intersects said irradiation field for said neutron radiation source and such that the inner side surface of each wedge-shaped slab is always directed generally towards said neutron radiation source; and at least one bearing means provided between each wedge-shaped slab and the respective individual carrier means on which it is movably mounted.

2. A neutron collimator in accordance with claim 1, in which each slab includes a bottom surface which is curved towards the effective neutron radiation source and further including bearing means including rollers housed in opposite slots, one slot being provided in said curved bottom surface of each slab, the other slot being provided in a complementary curved mounting bracket attached to said frame means.

3. A neutron collimator in accordance with claim 1, in which each slab is provided with a setting device for moving the slab along said respective carrier means.

4. A neutron collimator in accordance with claim 1 in which each slab includes a curved top surface, and in which a portion of the casing means faces the top curved surface of the slabs and has a complementary curved form.

5. A neutron collimator in accordance with claim 1, further including a lead glass slab movably mounted on guides provided in a bottom section of the frame means.

6. A neutron collimator in accordance with claim 1, in which said neutron radiation source includes a central beam directed along a plane, and the inner side surface of each slab is movable beyond the plane which contains the central beam of the effective neutron radiation source and which is perpendicular to all slab motion directions.

7. A neutron collimator in accordance with claim 1, and further including a mirror arranged in the beam path of said neutron radiation source and an illumination source positioned so that a bundle of light issued from the illumination source is reflected down through an opening confined by the inner side surfaces of the slabs as if the bundle of light virtually issued from the effective neutron radiation source.

8. A neutron collimator in accordance with claim 1, in which each wedge-shaped slab includes a mid-section, an outer side surface opposite to the respective inner side surface, opposite main surfaces, an opening extending between the opposite main surfaces of the respective slab and an aperture positioned near the center of gravity of the respective slab and extending through said outer side surface at the mid-section of the slab into said opening of the respective slab, and in which each individual carrier means includes an arm curved upwardly in the direction towards said neutron radiation source and extending into the aperture of the respective wedge-shaped slab which is mounted thereon.

9. A neutron collimator in accordance with claim 8, in which said at least one bearing means is provided at a top and bottom surface of each said arm, each bearing means associated with an arm and comprising a number of cylindrical rollers housed in opposite slots, one of said slots extending along a respective said arm and the other extending along a mounting bracket provided in said opening of a respective slab, said slots each having a square cross section and a curvature corresponding to that of the respective arm, the central axes of two adjacent rollers lying in spaced parallel planes and being perpendicular to each other.

10. A neutron collimator in accordance with claim 9, in which a plurality of said arms are connected to each other by rods extending through said openings in said slabs.

11. A neutron collimator in accordance with claim 8, in which the main surfaces of each slab are provided with first steps, the first steps on one main surface of each slab being complementary shaped to those of the other main surface, and in which opposite inner side surfaces of opposite slabs of a pair are provided with second steps, the second steps of one slab being complementary formed to that of the opposite slab in the pair.

12. A neutron collimator in accordance with claim 8, in which each slab includes second bearing means provided in and extending a small distance out from at least one main surface of the respective slab at top and bottom sections thereof.

13. A neutron collimator with an adjustable irradiation field for an effective neutron radiation source, comprising:

support means including a plurality of individual carrier means;

frame means in which said support means is mounted;

protective radiation casing means surrounding said frame means;

a plurality of pairs of opposite elongated wedge-shaped slabs arranged side by side such that respective ones of said opposite wedge-shaped slabs form a fan-shaped configuration which converges toward an apex at said neutron radiation source, each wedge-shaped slab having an inner side surface and being mounted for rotational and translational movement on a respective one of said individual carrier means such that the wedge-shaped slabs of each pair are mounted for motion towards and away from each other along a path which intersects said irradiation field for said neutron radiation source and such that the inner side surface of each wedge-shaped slab is always directed generally towards said neutron radiation source, and each wedge-shaped slab including a mid-section, an outer side surface opposite to the respective inner side surface, opposite main surfaces, an opening extending between the opposite main surfaces of the respective slab and an aperture positioned near the center of gravity of the respective slab and extending through said outer side surface at the mid-section of the slab into said opening of the respective slab, and in which each individual carrier means includes an arm curved upwardly in the direction towards said neutron radiation source and extending into the aperture of the respective wedge-shaped slab which is mounted thereon, the two main surfaces of each slab further being provided with second openings generally completely filled with a low density, high hydrogen atom content material, each slab having a top portion comprised at least of tungsten and the material in the remainder of the slab comprising at least one of steel and low carbon soft iron; and at least one bearing means provided between each wedge-shaped slab and the respective individual carrier means on which it is movably mounted.

* * * * *